(12) United States Patent
Chi et al.

(10) Patent No.: US 9,156,869 B2
(45) Date of Patent: Oct. 13, 2015

(54) RUTHENIUM COMPLEX FOR DYE-SENSITIZED SOLAR CELL

(71) Applicant: National Tsing Hua University, Hsinchu (TW)

(72) Inventors: Yun Chi, Hsinchu (TW); Chun-Cheng Chou, Hsinchu (TW); Fa-Chun Hu, Hsinchu (TW); Sheng-Wei Wang, Hsinchu (TW)

(73) Assignee: NATIONAL TSING HUA UNIVERSITY, Hsinchu (TW)

( * ) Notice: Subject to any disclaimer, the term of this patent is extended or adjusted under 35 U.S.C. 154(b) by 195 days.

(21) Appl. No.: 14/096,318

(22) Filed: Dec. 4, 2013

(65) Prior Publication Data

US 2014/0094606 A1 Apr. 3, 2014

Related U.S. Application Data

(63) Continuation-in-part of application No. 13/306,609, filed on Nov. 29, 2011, now Pat. No. 8,822,818.

(30) Foreign Application Priority Data

Apr. 1, 2011 (TW) .............................. 100111578 A
Jun. 20, 2013 (TW) .............................. 102121936 A

(51) Int. Cl.
| | | |
|---|---|---|
| *C07F 15/00* | (2006.01) | |
| *C07D 401/14* | (2006.01) | |
| *C07D 409/14* | (2006.01) | |
| *C07D 495/04* | (2006.01) | |
| *H01L 51/00* | (2006.01) | |
| *C09B 57/10* | (2006.01) | |
| *H01G 9/20* | (2006.01) | |

(52) U.S. Cl.
CPC .............. *C07F 15/00* (2013.01); *C07D 401/14* (2013.01); *C07D 409/14* (2013.01); *C07D 495/04* (2013.01); *C07F 15/0053* (2013.01); *C09B 57/10* (2013.01); *H01G 9/2059* (2013.01); *H01L 51/0086* (2013.01); *H01G 9/2031* (2013.01); *Y02E 10/542* (2013.01); *Y02E 10/549* (2013.01)

(58) Field of Classification Search
None
See application file for complete search history.

(56) References Cited

U.S. PATENT DOCUMENTS

| 7,812,251 B2 * | 10/2010 | Islam et al. ................. 136/263 |
| 2005/0081911 A1 | 4/2005 | Islam et al. |
| 2009/0107552 A1 | 4/2009 | Minns et al. |
| 2010/0010643 A1 | 1/2010 | Pomerantz et al. |
| 2010/0258175 A1 | 10/2010 | Chi et al. |
| 2012/0247561 A1 | 10/2012 | Chi et al. |

FOREIGN PATENT DOCUMENTS

| TW | 201240988 A1 | 10/2012 |
| TW | 1379836 B1 | 12/2012 |

* cited by examiner

*Primary Examiner* — Kamal Saeed
(74) *Attorney, Agent, or Firm* — Birch, Stewart, Kolasch & Birch, LLP

(57) ABSTRACT

A ruthenium complex for a dye-sensitized solar cell includes a chemical formula represented by Formula (I):

$$RuL^1L^2L^3 \quad (I)$$

where
$L^1$ represents a monodentate ligand;
$L^2$ represents a tridentate ligand of

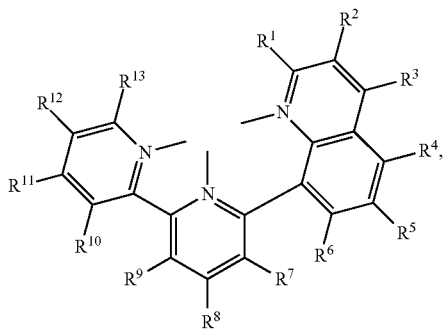

and
$L^3$ represents a bidentate ligand of

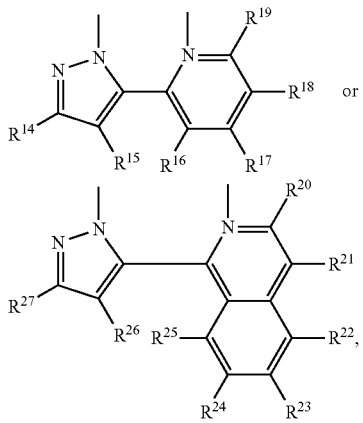

where $R^1$ to $R^{27}$ have meaning as defined in the specification.

6 Claims, 2 Drawing Sheets

RUTHENIUM COMPLEX FOR DYE-SENSITIZED SOLAR CELL

CROSS-REFERENCE TO RELATED APPLICATION

This application is a continuation-in-part of co-pending U.S. patent application Ser. No. 13/306,609, filed on Nov. 29, 2011, which claims priority of Taiwanese Application No. 100111578 filed on Apr. 1, 2011. This application also claims priority to Taiwanese Application No. 102121936 filed on Jun. 20, 2013. These applications are hereby expressly incorporated by reference into the present application.

BACKGROUND OF THE INVENTION

1. Field of the Invention

This invention relates to a ruthenium complex, more particularly to a ruthenium complex for a dye-sensitized solar cell.

2. Description of the Related Art

Photovoltaic cells, sometimes called solar cells, are being increasingly developed in the art due to the fact that sunlight to be converted into electrical energy via the photovoltaic cells is inexhaustible. A dye-sensitized solar cell (DSSC) is one of the photovoltaic cells having most potential. The dye contained in the DSSC is used to absorb visible and near infrared light from the sun to excite electrons. The excited electrons are then injected into a conduction band of a semiconductor electrode so as to produce photocurrent. Therefore, the photovoltaic conversion efficiency of the DSSC is affected primarily by the performance of the dye. Ruthenium complex is primarily searched and developed as a dye commonly used in the dye-sensitized solar cell.

US 2010/0258175A1 discloses a photosensitizer complex represented by formula (a):

MXYZ  (a)

where

M represents ruthenium,

X represents a monodentate anion ligand selected from halide, pseudohalide, carboxylate, carbanion, sulfate, phosphate, thiocyanate, and other organic anion, Y represents a heterocyclic bidentate ligand including a structural formula represented by Formula (b) or Formula (c) listed below:

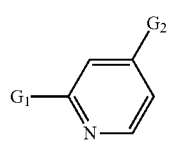

(b)

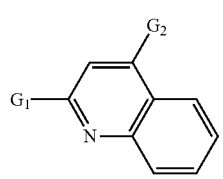

(c)

where $G_1$ comprises a structural formula represented by Formula (d), Formula (e), Formula (f), or Formula (g) listed below:

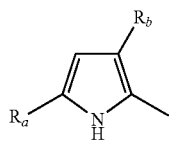

(d)

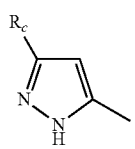

(e)

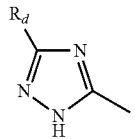

(f)

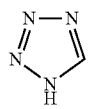

(g)

$G_2$ comprises a structural formula represented by Formula (h), Formula (I), or Formula (j) listed below:

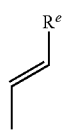

(h)

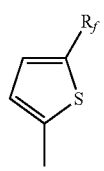

(i)

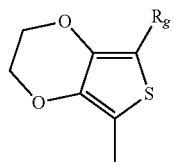

(j)

Z represents a tridentate ligand including a structural formula represented by Formula (k) listed below:

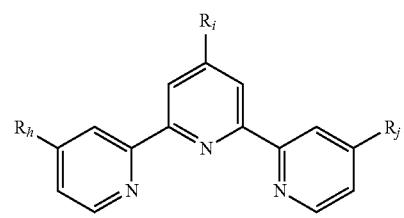

(k)

where
$R_a$, $R_b$, $R_c$, $R_d$, $R_e$, $R_f$, $R_g$, $R_h$, $R_i$, and $R_j$ are the same or different, and represent a $C_1$-$C_8$ alkyl group, a $C_1$-$C_8$ alkoxyl group, a $C_1$-$C_8$ alkylthio group, a $C_1$-$C_8$ alkylamino group, a $C_1$-$C_8$ halogenated alkyl group, a phenyl group or a substituted phenyl group containing $C_1$-$C_6$ alkyl or alkoxyl group, a triphenylamino group or a substituted triphenylamino group containing a $C_1$-$C_6$ alkyl or alkoxyl group, a carboxylic acid group or a carboxylate group, a sulfonic acid group or a sulfonate group, a phosphoric acid group or a phosphate group, an amino group, halogen, or hydrogen; or $R_c$ and $R_d$ comprise a structural formula represented by Formula (m) listed below:

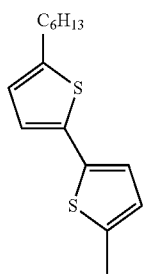

(m)

A photosensitizer complex disclosed in US 2010/0258175A1 is represented by the following Formula (n):

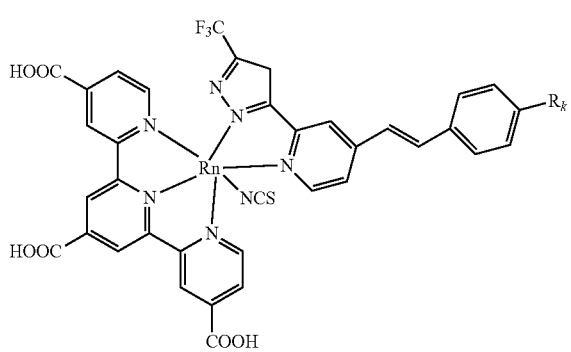

(n)

where
$R_k$ represents hydrogen, $OCH_3$, $OC_8H_{17}$, or an isobutyl group. When the photosensitizer complex of Formula (n) is utilized in the dye-sensitized solar cell, the dye-sensitized solar cell has an open circuit voltage ranging from 668 V to 720 V, a short circuit current density ranging from 20.3 $mAcm^{-2}$ to 21.7 $mAcm^{-2}$, and a photovoltaic conversion efficiency ranging from 9.14% to 10.05%. However, the demand for the photovoltaic conversion efficiency of the dye-sensitized solar cell is always increasing, and the photosensitizer complex disclosed in US 2010/0258175A1 may not meet current industrial requirements.

SUMMARY OF THE INVENTION

Therefore, an object of the present invention is to provide a ruthenium complex which has good photovoltaic conversion efficiency and which is adapted for a dye-sensitized solar cell.

According to this invention, there is provided a ruthenium complex for a dye-sensitized solar cell. The ruthenium complex includes a chemical formula represented by Formula (I):

$$RuL^1L^2L^3 \quad (I)$$

where
$L^1$ represents a monodentate ligand;
$L^2$ represents a tridentate ligand of

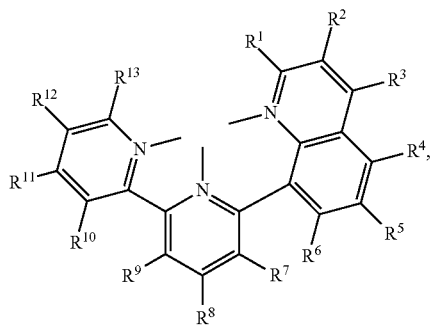

where
$R^1$, $R^2$, $R^3$, $R^4$, $R^5$, and $R^6$ independently represent hydrogen, isobutyl,

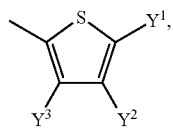

—$N(Ar)_2$, or —Ar—$N(Ar)_2$, where $Y^1$, $Y^2$, and $Y^3$ independently represent hydrogen, —$N(Ar)_2$, or —Ar—$N(Ar)_2$, and Ar represents an aryl group, and
$R^7$, $R^8$, $R^9$, $R^{10}$, $R^{11}$, $R^{12}$, and $R^{13}$ independently represent hydrogen, halogen, trifluoromethyl, a $C_1$-$C_{12}$ straight chain alkyl group, a $C_1$-$C_{12}$ branched chain alkyl group, a phosphoric acid group, a phosphate group, a boric acid group, a borate group, a sulfonic acid group, a sulfonate group, a carboxylic acid group, or a carboxylate group with the proviso that at least two of $R^7$, $R^8$, $R^9$, $R^{10}$, $R^{11}$, $R^{12}$, and $R^{13}$ represent a carboxylic acid group or a carboxylate group;
and
$L^3$ represents a bidentate ligand of

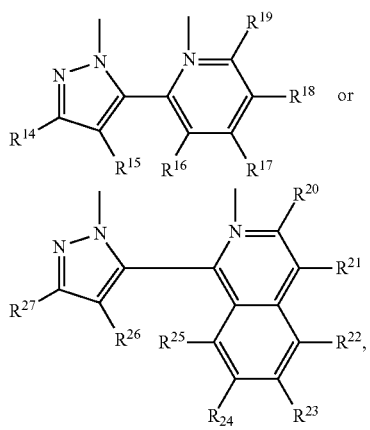

where
$R^{14}$ and $R^{27}$ independently represent a fluoroalkyl group, and
$R^{15}$, $R^{16}$, $R^{17}$, $R^{18}$, $R^{19}$, $R^{20}$, $R^{21}$, $R^{22}$, $R^{23}$, $R^{24}$, $R^{25}$, and $R^{26}$ independently represent hydrogen, isobutyl,

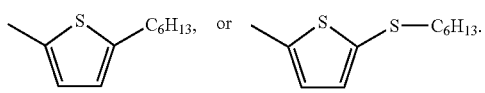

BRIEF DESCRIPTION OF THE DRAWINGS

Other features and advantages of the present invention will become apparent in the following detailed description of the preferred embodiments with reference to the accompanying drawings, of which.

DETAILED DESCRIPTION OF THE PREFERRED EMBODIMENTS

Figure 1:
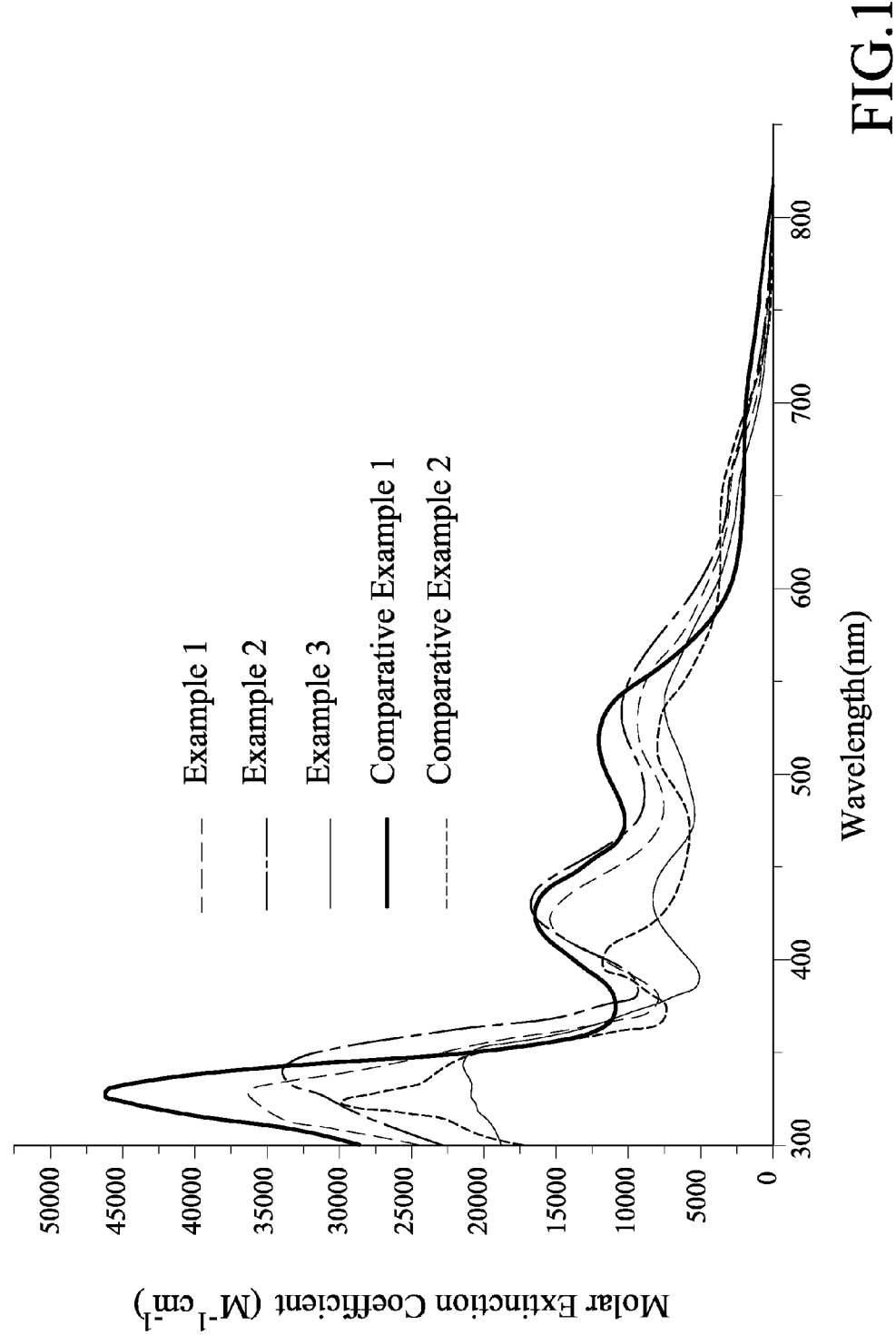
FIG. 1 is a graph to illustrate the absorption spectra of ruthenium complexes of Examples of this invention and Comparative Examples 1 and 2.
Figure 2:
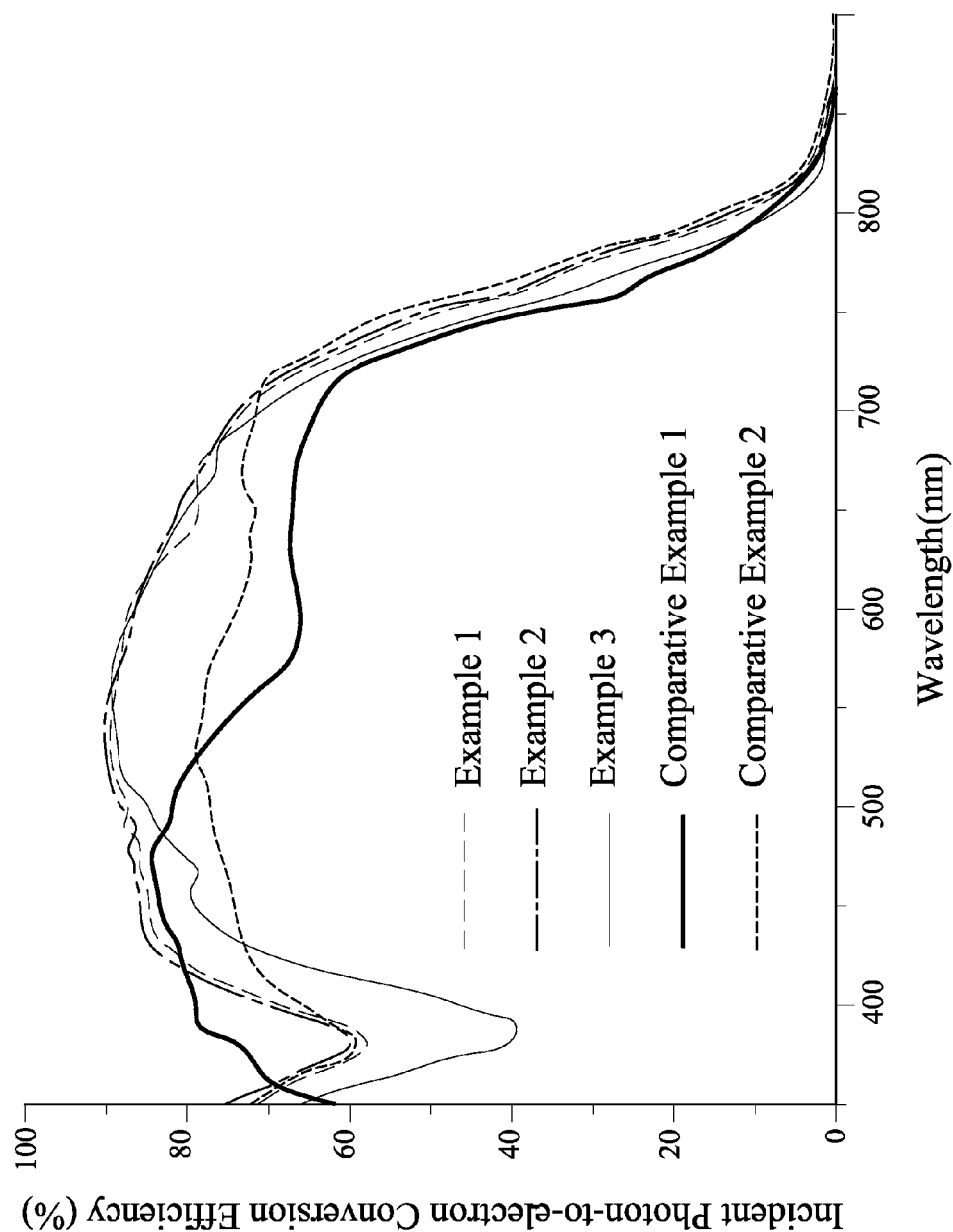
FIG. 2 is a graph to illustrate incident photon-to-electron conversion efficiencies of dye-sensitized solar cells including the ruthenium complexes of the Examples of the present invention and Comparative Examples 1 and 2.

A ruthenium complex for a dye-sensitized solar cell according to this invention includes a chemical formula represented by Formula (I):

where
$L^1$ represents a monodentate ligand;
$L^2$ represents a tridentate ligand of

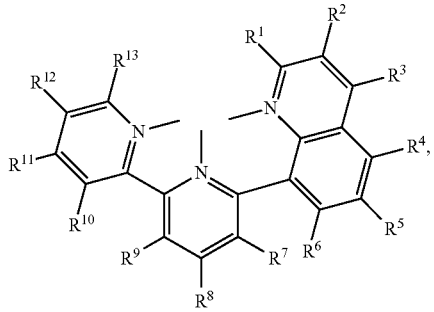

where
$R^1$, $R^2$, $R^3$, $R^4$, $R^5$, and $R^6$ independently represent hydrogen, isobutyl,

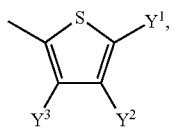

—$N(Ar)_2$, or —Ar—$N(Ar)_2$, where $Y^1$, $Y^2$, and $Y^3$ independently represent hydrogen, —$N(Ar)_2$, or —Ar—N$(Ar)_2$, and Ar represents an aryl group, and
$R^7$, $R^8$, $R^9$, $R^{10}$, $R^{11}$, $R^{12}$, and $R^{13}$ independently represent hydrogen, halogen, trifluoromethyl, a $C_1$-$C_{12}$ straight chain alkyl group, a $C_1$-$C_{12}$ branched chain alkyl group, a phosphoric acid group, a phosphate group, a boric acid group, a borate group, a sulfonic acid group, a sulfonate group, a carboxylic acid group, or a carboxylate group with the proviso that at least two of $R^7$, $R^8$, $R^9$, $R^{10}$, $R^{11}$, $R^{12}$, and $R^{13}$ represent a carboxylic acid group or a carboxylate group;
and
$L^3$ represents a bidentate ligand of

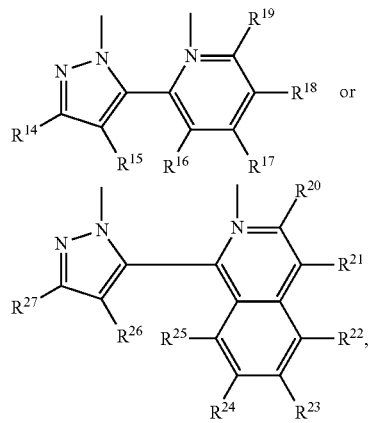

where
$R^{14}$ and $R^{27}$ independently represent a fluoroalkyl group, and
$R^{15}$, $R^{16}$, $R^{17}$, $R^{18}$, $R^{19}$, $R^{20}$, $R^{21}$, $R^{22}$, $R^{23}$, $R^{24}$, $R^{25}$, and $R^{26}$ independently represent hydrogen, isobutyl,

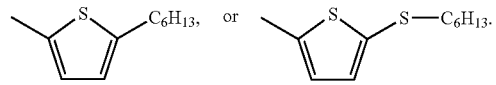

Preferably, $R^1$, $R^2$, $R^3$, $R^4$, $R^5$, and $R^6$ are not hydrogen at the same time.

Preferably, the fluoroalkyl group represents $C_nF_{2n+1}$, where n is an integer ranging from 1 to 7.

Preferably, the monodentate ligand includes —N=C=S.

Preferably, at least one of $R^{16}$, $R^{17}$, $R^{18}$, and $R^{19}$ is

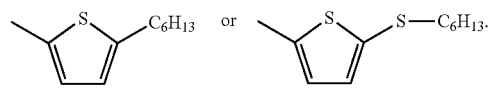

Preferably, at least one of $R^{20}$, $R^{21}$, $R^{22}$, $R^{23}$, $R^{24}$, and $R^{25}$ represents isobutyl.

In the preferred embodiment according to this invention, $L^2$ represents a structural formula of

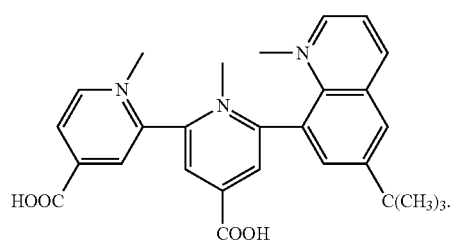

In the preferred embodiment according to this invention, $L^3$ represents a structural formula of

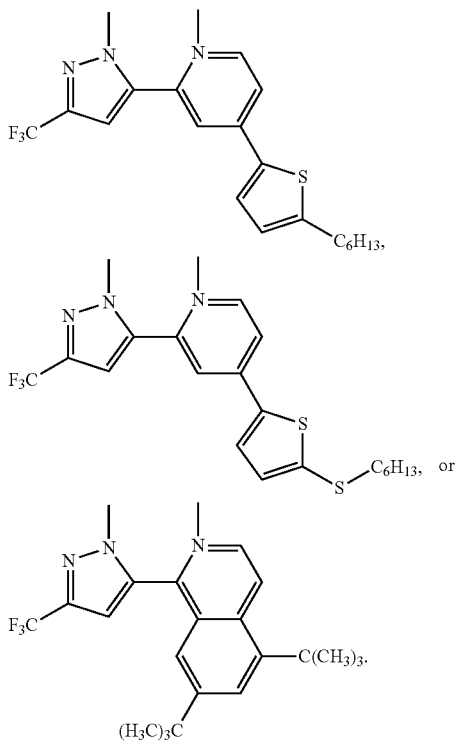

The proper reactants and reaction conditions for preparing the ruthenium complex for the dye-sensitized solar cell may be selected based on the ligands of the ruthenium complex. The preparation of the ruthenium complex of the present invention may be conducted in a manner well known in the art. It should be noted that, in the following description, the substituents of the reactants are assigned in a manner identical to that for the substituents of the ligands $L^1$, $L^2$, and $L^3$.

The ruthenium complex for the dye-sensitized solar cell according to this invention may be prepared by the following steps: (1) mixing the tridentate compound represented by Formula (II) with the ruthenium source and heating them to react; (2) adding the bidentate compound represented by Formulas (III) or (IV), heating in the presence of a catalyst to react; and (3) adding the monodentate compound to react so as to obtain the ruthenium complex for the dye-sensitized solar cell;

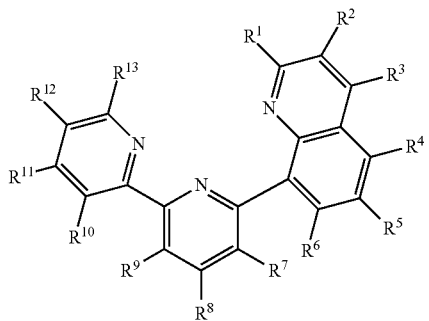

(II)

where
$R^1$, $R^2$, $R^3$, $R^4$, $R^5$, and $R^6$ independently represent hydrogen, isobutyl,

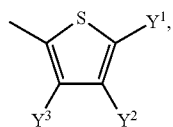

—N(Ar)$_2$, or —Ar—N(Ar)$_2$, where $Y^1$, $Y^2$, and $Y^3$ independently represent hydrogen, —N(Ar)$_2$, or —Ar—N(Ar)$_2$, and Ar represents an aryl group, and $R^7$, $R^8$, $R^9$, $R^{10}$, $R^{11}$, $R^{12}$, and $R^{13}$ independently represent hydrogen, halogen, trifluoromethyl, a $C_1$-$C_{12}$ straight chain alkyl group, a $C_1$-$C_{12}$ branched chain alkyl group, a phosphoric acid group, a phosphate group, a boric acid group, a borate group, a sulfonic acid group, a sulfonate group, a carboxylic acid group, or a carboxylate group with the proviso that at least two of $R^7$, $R^8$, $R^9$, $R^{10}$, $R^{11}$, $R^{12}$, and $R^{13}$ represent a carboxylic acid group or a carboxylate group;

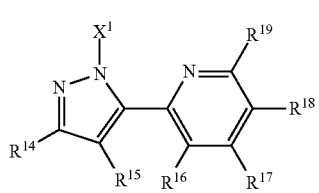

(III)

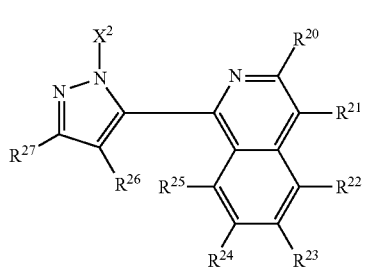

(IV)

where
$X^1$ and $X^2$ independently represent hydrogen,
$R^{14}$ and $R^{27}$ independently represent a fluoroalkyl group, and
$R^{15}$, $R^{16}$, $R^{17}$, $R^{18}$, $R^{19}$, $R^{20}$, $R^{21}$, $R^{22}$, $R^{23}$, $R^{24}$, $R^{25}$, and $R^{26}$ independently represent hydrogen, isobutyl,

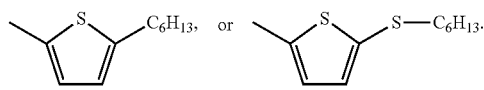

Preferably, the ruthenium source is RuCl$_3$·3H$_2$O.
Preferably, the monodentate compound is potassium thiocyanate.
Preferably, the catalyst is potassium acetate (referred as KOAc) or sodium acetate.

This invention also provides a dye-sensitized solar cell which includes an electrolytic component, a first electrode, and a second electrode. The first electrode is disposed in the electrolytic component, and includes a transparent conductive substrate and a porous film disposed on a surface of the transparent conductive substrate. The porous film adsorbs the abovementioned ruthenium complex. The second electrode is spaced apart from the first electrode and is disposed in the electrolytic component.

The electrolytic component includes, but is not limited to, a mixture solution containing iodine and iodic ions in a solvent consisting of valeronitrile and acetonitrile (v/v=15:85), a mixture solution containing 1,3-dimethylimidazolium iodide (referred as DMII, 0.6 M), lithium iodide (referred as LiI, 0.1 M), $I_2$ (0.05 M), and tert-butylpyridine (0.5 M) dissolved in acetonitrile, or a mixture solution containing DMII (0.5 M), LiI (0.1 M), $I_2$ (0.1 M), and tert-butylpyridine (0.5 M) dissolved in acetonitrile.

Preferably, the material for the transparent conductive substrate is a flexible polymeric material or a rigid material. Examples of the flexible polymeric material include, but are not limited to, polyethylene, polypropylene, polyimide, polymethyl methacrylate, polycarbonate, polyethylene terephthalate, or the like. Examples of the rigid material include, but are not limited to, glass, or the like. Preferably, the material for the porous film is selected from titanium dioxide (referred as $TiO_2$), zinc oxide, tin oxide, or the like.

The method for manufacturing the dye-sensitized solar cell is well known in the art, and thus is not described in detail herein.

The following examples are provided to illustrate the preferred embodiments of the invention, and should not be construed as limiting the scope of the invention.

EXAMPLES

Example 1

$RuCl_3 \cdot 3H_2O$ (50 mg, 0.19 mmol),

(95 mg, 0.19 mmol), and ethanol (30 mL) were added into a 50 mL round-bottom flask, and were heated under reflux for 4 hours. After the reaction was completed, the temperature in the flask was reduced to room temperature, and a filter cake was obtained via filtering. The filter cake was washed using ethanol and then dried.

The abovementioned filter cake,

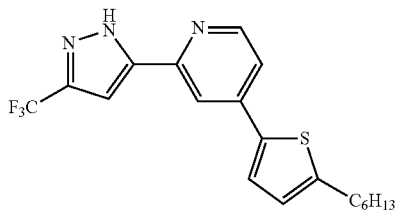

(72 mg, 0.19 mmol), potassium acetate (37 mg, 0.38 mmol), and toluene (30 mL) were added into the 50 mL round-bottom flask, and were heated under reflux for 8 hours. After the reaction was completed, toluene was removed. Subsequently, N,N-dimethylformamide (30 mL) and potassium thiocyanate (185 mg, 1.9 mmol) were added and heated with stirring at 110° C. for 2 hours, and N,N-dimethylformamide was then removed. Column chromatography was conducted using dichloromethane and ethyl acetate as eluent (dichloromethane:ethyl acetate=10:1), and a reddish black solid was obtained. The reddish black solid, acetone, and NaOH solution (1 M) were mixed to produce a solid which was collected and washed using water and acetone sequentially to obtain a ruthenium complex (referred as complex A-1 hereinafter, 73 mg, yield: 40%).

Spectral analysis data of the complex A-1: $^1H$ NMR (400 MHz, $d_6$-DMSO, 298 K), δ (ppm): 9.08 (s, 1H), 9.01 (d, $J_{HH}$=6.0 Hz, 1H), 8.99 (s, 1H), 8.69 (s, 1H), 8.61 (s, 1H), 8.43 (d, $J_{HH}$=8.0 Hz, 1H), 8.27 (s, 1H), 8.26 (s, 1H), 8.15 (s, 1H), 7.94-7.90 (m, 3H), 7.74 (d, $J_{HH}$=6.0 Hz, 1H), 7.37-7.34 (m, 1H), 7.04 (s, 2H), 2.88 (t, $J_{HH}$=8.0 Hz, 2H), 1.65 (m, 2H), 1.53 (s, 9H), 1.34-1.28 (m, 6H), 0.86 (t, $J_{HH}$=8.0 Hz, 3H). $^{19}F$ NMR (376 MHz, $d_6$-DMSO, 298 K), δ (ppm): δ −56.01 (s, 3F). MS (FAB, $^{102}Ru$): m/z 966 (M+1)$^+$. The chemical structure of the complex A-1 was confirmed to be

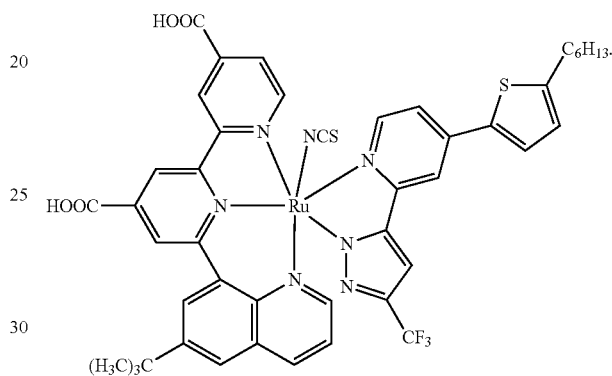

Example 2

$RuCl_3 \cdot 3H_2O$ (50 mg, 0.19 mmol),

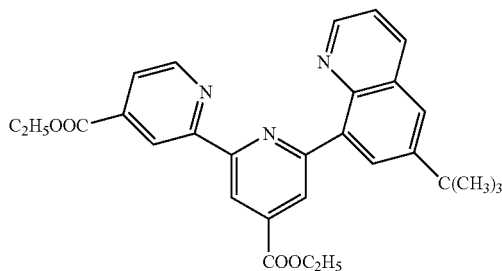

(95 mg, 0.19 mmol), and ethanol (30 mL) were added into a 50 mL round-bottom flask, and were heated under reflux for 4 hours. After the reaction was completed, the temperature in the flask was reduced to room temperature, and a filter cake was obtained via filtering. The filter cake was washed using ethanol and then dried.

The abovementioned filter cake,

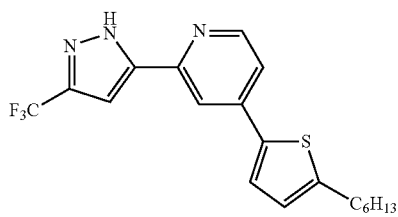

(78 mg, 0.19 mmol), potassium acetate (37 mg, 0.38 mmol), and toluene (30 mL) were added into the 50 mL round-bottom flask, and were heated under reflux for 8 hours. After the reaction was completed, toluene was removed. Subsequently, N,N-dimethylformamide (30 mL) and potassium thiocyanate (185 mg, 1.9 mmol) were added and heated with stirring at 110° C. for 2 hours, and N,N-dimethylformamide was then removed. Column chromatography was conducted using dichloromethane and ethyl acetate as eluent (dichlormethane:ethyl acetate=10:1), and a reddish black solid was obtained. The reddish black solid, acetone (1 mL), and NaOH solution (1 M) were mixed to produce a solid which was collected and washed using water and acetone sequentially to obtain a ruthenium complex (referred as complex A-2 hereinafter, 73 mg, yield: 42%).

Spectral analysis data of the complex A-2: $^1$H NMR (400 MHz, d$_6$-DMSO, 298 K), δ (ppm): 9.12 (s, 1H), 9.06 (d, J$_{HH}$=6.0 Hz, 1H), 9.03 (s, 1H), 8.72 (s, 1H), 8.65 (s, 1H), 8.47 (d, J$_{HH}$=8.0 Hz, 1H), 8.34 (s, 1H), 8.28 (d, J$_{HH}$=6.0 Hz, 1H), 8.18 (s, 1H), 8.04-7.99 (m, 2H), 7.93 (d, J$_{HH}$=6.0 Hz, 1H), 7.76 (d, J$_{HH}$=6.0 Hz, 1H), 7.40-7.35 (m, 2H), 7.04 (s, 1H), 2.99 (t, J$_{HH}$=8.0 Hz, 2H), 1.63 (m, 2H), 1.47 (s, 9H), 1.43-1.25 (m, 6H), 0.87 (t, J$_{HH}$=8.0 Hz, 3H). $^{19}$F NMR (376 MHz, d$_6$-DMSO, 298 K), δ (ppm): −58.86 (s, 3F). MS (FAB, $^{102}$Ru): m/z 966 (M+1)$^+$. The chemical structure of the complex A-2 was confirmed to be

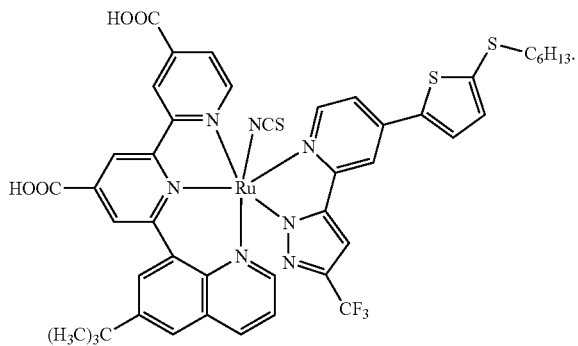

Example 3

RuCl$_3$·3H$_2$O (50 mg, 0.19 mmol),

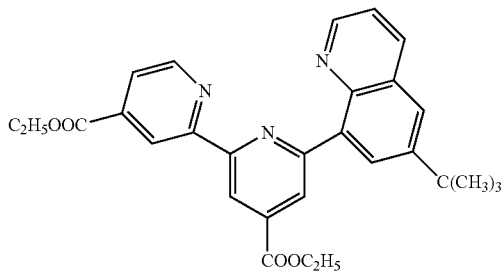

(95 mg, 0.19 mmol), and ethanol (30 mL) were added into a 50 mL round-bottom flask, and were heated under reflux for 4 hours. After the reaction was completed, the temperature in the flask was reduced to room temperature, and a filter cake was obtained via filtering. The filter cake was washed using ethanol and then dried.

The abovementioned filter cake,

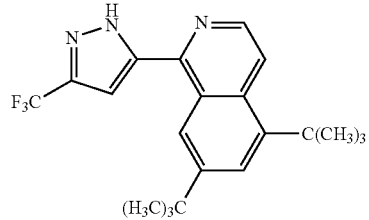 [SMILES: CC(C)(C)c1cc(C(C)(C)C)c2ccnc(-c3cc(C(F)(F)F)n[nH]3)c2c1]

(71 mg, 0.19 mmol), potassium acetate (37 mg, 0.38 mmol), and toluene (30 mL) were added into the 50 mL round-bottom flask, and were heated under reflux for 8 hours. After the reaction was completed, toluene was removed. Subsequently, N,N-dimethylformamide (30 mL) and potassium thiocyanate (185 mg, 1.9 mmol) were added and heated with stirring at 110° C. for 2 hours, and N,N-dimethylformamide was then removed. Column chromatography was conducted using dichloromethane and ethyl acetate as eluent (dichloromethane:ethyl acetate=10:1), and a reddish black solid was obtained. The reddish black solid, acetone (1 mL), and NaOH solution (1 M) were mixed to produce a solid which was collected and washed using water and acetone sequentially to obtain a ruthenium complex (referred as complex A-3 hereinafter, 65 mg, yield: 360).

Spectral analysis data of the complex A-3: $^1$H NMR (400 MHz, d$_6$-DMSO, 298 K), δ (ppm): 9.17 (d, J$_{HH}$=6.0 Hz, 1H), 9.16 (s, 1H), 9.05 (s, 1H), 8.74 (s, 1H), 8.67 (s, 1H), 8.65 (d, J$_{HH}$=8.0 Hz, 1H), 8.43 (d, J$_{HH}$=6.0 Hz, 1H), 8.41 (s, 1H), 8.20 (d, J$_{HH}$=6.0 Hz, 1H), 8.17 (s, 1H), 7.95 (s, 1H), 7.76 (d, J$_{HH}$=6.0 Hz, 1H), 7.72 (d, J$_{HH}$=6.0 Hz, 1H), 7.29-7.26 (m, 1H), 6.99 (s, 1H), 1.73 (s, 9H), 1.51 (s, 9H), 1.42 (s, 9H). $^{19}$F NMR (376 MHz, d$_6$-DMSO, 298 K), δ (ppm): −59.02 (s, 3F). MS (FAB, $^{102}$Ru): m/z 992 (M+1)$^+$. The chemical structure of the complex A-3 was confirmed to be

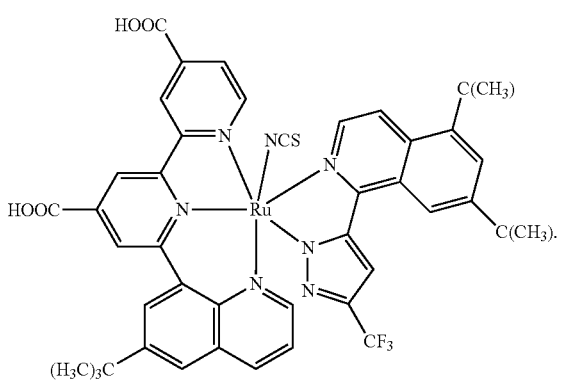

Comparative Example 1

A photosensitizer complex PRT4 disclosed in US 2010/0258175A1 was prepared.

Comparative Example 2

A ruthenium complex disclosed in Example 3 in US 2012/0247561A1 was prepared.

[Test Items]

1. Measurement of Molar Extinction Coefficient (Hereinafter Referred to as ε):

Each of the ruthenium complexes of Examples 1 to 3 and Comparative Examples 1 and 2 was dissolved in N,N-dimethylformamide to obtain a sample solution having a concentration of $1\times10^{-5}$ M, followed by measuring molar extinction coefficient thereof using a UV-Visible spectrophotometer (Hitachi Spectrophotometer; Model no.: U-3900). The data is shown in Table 1, Table 2, and FIG. 1.

2. Measurement of Photovoltaic Conversion Efficiency:

It is noted that the manufacturing process of a dye-sensitized solar cell is well known in the art and the following examples are used for illustration, and should not be construed as limiting the implementation of the present invention.

Preparation of Dye-Sensitized Solar Cells:

First Electrode:

A fluorine-doped tin oxide conductive glass ($15\times15$ mm$^2$, thickness: 3.2 mm, sheet resistance: 9 Ω/cm$^2$) was washed using a cleaning agent, water, acetone, and ethanol, followed by placing in an ultra-violet ozone device for 15 minutes. Thereafter, TiO$_2$ nanoparticles (20 nm) were applied on the fluorine-doped tin oxide conductive glass as a dye adsorption layer by means of a screen printing process in an applied surface area of 0.25 cm$^2$. Similarly, TiO$_2$ nanoparticles (400 nm) were applied on the dye adsorption layer by means of the screen printing process in an applied surface area of 0.25 cm$^2$, followed by thermal cracking at 325° C. for 30 minutes, at 375° C. for 5 minutes, at 450° C. for 15 minutes, and at 500° C. for 3 minutes in sequence. Finally, an adsorption layer (thickness: 15 μm) and a scattering layer (thickness: 7 μm) were formed. After cooling, the fluorine-doped tin oxide conductive glass applied with the TiO$_2$ nanoparticles was immersed in a titanium tetrachloride aqueous solution (40 mM) at 70° C. for 30 minutes and rinsed with water and ethanol, followed by thermal cracking at 500° C. for 30 minutes to form a conductive substrate containing TiO$_2$. After the conductive substrate was cooled to 80° C., the same was immersed in a mixed solution for 18 hours to form a first electrode. The mixed solution contains the ruthenium complex of the present invention, of Comparative Example 1, or of Comparative Example 2 ($3\times10^{-4}$ M), tetra-n-butylammonium deoxycholate ($6\times10^{-4}$ M), deoxycholic acid ($10\times10^{-4}$ M), n-butyl alcohol, and ethanol.

Second Electrode:

A H$_2$PtCl$_6$ solution in isopropanol (10 μL, 50 mM) was dropped onto each of five fluorine-doped tin oxide conductive glasses ($15\times15$ mm$^2$), followed by thermal cracking at 400° C. for 15 minutes to obtain a second electrode.

Electrolytic Component:

An electrolytic component is the mixture solution containing DMII (0.6 M), LiI (0.1 M), I$_2$ (0.05 M), and tert-butylpyridine (0.5 M) dissolved in acetonitrile.

The first and second electrodes were packaged in pairs using a hot melting polymer film, and the electrolytic component (10 μL) was injected via a pre-drilled small hole in the second electrode. Next, the small hole was sealed using the hot melting polymer film and a small piece of glass, thereby obtaining the dye-sensitized solar cells.

Method 1:

Each of the dye-sensitized solar cells was covered with a light-shield plate of stainless steel with an irradiation area of $4\times4$ mm$^2$ for exposing the dye-sensitized solar cell. The irradiation area of each of the dye-sensitized solar cells was irradiated by a solar simulator (150 W xenon lamp; Class A, Newport Oriel; Model no.: 91159) that provides a simulation light with air mass (AM) 1.5 Global spectrum and an intensity of 100 mW/cm$^2$. (The simulation light is defined by calibrating a standard solar cell with a KG-5 filter). An external voltage was applied to each of the dye-sensitized solar cells using an external digital electrometer (Keithley; Model no.: 2400), and the short circuit current density of each of the dye-sensitized solar cells was recorded. Data were collected to plot a graph of voltage vs. short circuit current density. In the graph of voltage vs. short circuit current density, an open circuit voltage when a current density is 0 and a short circuit current density when a voltage is 0 were obtained to evaluate the photovoltaic conversion efficiency (η). Specifically, the photovoltaic conversion efficiency (η) is obtained by dividing the maximum value of the product of the open circuit voltage and the short circuit current density by the value of the incident light intensity. The data is shown in Tables 1 and 2.

Method 2:

The differences between Method 1 and Method 2 are listed below:

(1) The dye-sensitized solar cells were not covered with a light-shield plate of stainless steel and exposed directly to the solar simulator, and had an irradiation area of $4\times4$ mm$^2$;

(2) TiO$_2$ porous membrane included an adsorption layer and a scattering layer, wherein the adsorption layer had a thickness of 18 μm and was made from the TiO$_2$ nanoparticles (20 nm), and the scattering layer had a thickness of 4 μm and was made from the TiO$_2$ nanoparticles (400 nm);

(3) A Mixture Solution of the electrolytic component contained DMII (0.6 M), LiI (0.1 M), I$_2$ (0.1 M), and tert-butylpyridine (0.5M) dissolved in acetonitrile. The data is shown in Tables 1 and 2. Comparative Example 1 was measured using Method 2, and the mixture solution contained the ruthenium complex in Comparative Example 1, deoxycholic acid, n-butyl alcohol, and dimethylformamide. In this mixture solution, the concentration of the ruthenium complex was $3\times10^{-4}$ M.

3. Measurement of Incident Photon-to-Electron Conversion Efficiency (Hereinafter Referred to as IPCE):

Unchopped monochromatic beam was provided using a light source (300 W xenon lamp; Newport Oriel; Model no.: 6258) and a monochromator (Oriel cornerstone; Model no.: Oriel cornerstone 260 ¼ m monochromator 74100) to irradiate each of the dye-sensitized solar cells. IPCE is calculated using the following formula:

$$\text{IPCE}(\lambda) = \text{LHE}(\lambda) \times \phi_{inj} \times \eta_c = [1240 \times J_{SC}(\lambda)] / [\lambda \times P_{in}(\lambda)]$$

where

LHE(λ) (light harvesting efficiency): light absorption rate at a specific wavelength;

$\phi_{inj}$: quantum yield of injected electron;

$\eta_c$: dissolution rate of electric charge;

$J_{sc}(\lambda)$: photo-current density generated by being irradiated at a specific wavelength;

λ: incident wavelength;

$P_{in}(\lambda)$: incident light intensity.

TABLE 1

| Ruthenium Complex | | UV Absorption Spectrum | | IPCE Integral Area (Theoretical Short Circuit Current Density) | Measuring Method | Photovoltaic conversion efficiency | | | |
|---|---|---|---|---|---|---|---|---|---|
| | | Wavelength (nm) | ε (×10³) | | | Short Circuit Current Density (mA cm⁻²) | Open circuit voltage (mV) | Filling factor (FF) | η (%) |
| Examples | 1 | 327 | 36.2 | 19.58 | Method 1 | 20.00 | 720 | 0.72 | 10.53 |
| | | 419 | 15.3 | | | | | | |
| | | 540 | 9.5 | | Method 2 | 22.06 | 740 | 0.68 | 11.10 |
| | | 671 | 2.6 | | | | | | |
| | 2 | 338 | 34.0 | 20.52 | Method 1 | 21.57 | 720 | 0.73 | 11.19 |
| | | 430 | 16.8 | | | | | | |
| | | 541 | 10.6 | | Method 2 | 22.68 | 750 | 0.69 | 11.81 |
| | | 671 | 2.6 | | | | | | |
| | 3 | 342 | 21.4 | 18.59 | Method 1 | 19.51 | 730 | 0.74 | 10.48 |
| | | 435 | 8.2 | | | | | | |
| | | 542 | 7.1 | | Method 2 | 21.52 | 750 | 0.69 | 11.17 |
| | | 661 | 2.1 | | | | | | |

TABLE 2

| Ruthenium Complex | | UV Absorption Spectrum | | IPCE Integral Area (Theoretical Short Circuit Current Density) | Measuring Method | Photovoltaic conversion efficiency | | | |
|---|---|---|---|---|---|---|---|---|---|
| | | Wavelength (nm) | ε (×10³) | | | Short Circuit Current Density (mA cm⁻²) | Open circuit voltage (mV) | Filling factor (FF) | η (%) |
| Comparative Examples | 1 | 328 | 46.4 | 19.49 | Method 1 | — | — | — | — |
| | | 424 | 16.6 | | Method 2 | 21.6 | 714 | 0.652 | 10.05 |
| | | 519 | 12.2 | | | | | | |
| | 2 | 323 | 29.9 | 18.02 | Method 1 | 19.3 | 650 | 0.7 | 8.76 |
| | | 401 | 12.0 | | Method 2 | 21.03 | 680 | 0.66 | 9.40 |
| | | 519 | 8.1 | | | | | | |
| | | 688 | 3.2 | | | | | | |

As shown in Table 1, Method 2 for measuring the photovoltaic conversion efficiency is a conventional measuring method. Each of the ruthenium complexes for the dye-sensitized solar cells of Examples 1 to 3 according to this invention was measured using the conditions of Method 2 so as to obtain the short circuit current density ranging from 21.52 mAcm⁻² to 22.68 mAcm⁻² and the photovoltaic conversion efficiency ranging from 11.10% to 11.81%. Referring to Comparative Example 1, the photosensitizer complex of Formula (n) disclosed in US 2010/0258175A1 is used in the dye-sensitized solar cell and was measured using Method 2 so as to obtain the short circuit current density being 21.6 mAcm⁻² and the photovoltaic conversion efficiency being 10.05%. The short circuit current density and the photovoltaic conversion efficiency are significantly improved in the present invention.

As shown in Table 1, Method 1 for measuring the photovoltaic conversion efficiency is a more exact measuring method, and the short circuit current density measured therethrough is close to a theoretical short circuit current density. Each of the ruthenium complexes for the dye-sensitized solar cells of Examples 1 to 3 according to this invention was measured using the conditions of Method 1 so as to obtain the short circuit current density ranging from 19.51 mAcm⁻² to 21.57 mAcm⁻² and the photovoltaic conversion efficiency ranging from 10.48% to 11.19%. Referring to Comparative Example 2, the metal complex of Example 3 disclosed in US 2012/0247561A1 is used in the dye-sensitized solar cell and was measured using Method 1 so as to obtain the short circuit current density being 19.3 mAcm⁻² and the photovoltaic conversion efficiency being 8.76%. The photovoltaic conversion efficiency is significantly improved in the present invention.

The applicant would like to point out that N719 and N749 have been proposed by Professor Michael Grätzel for more than a decade, and that the ruthenium complexes similar to N719 and N749 are used in the dye-sensitized solar cell and the photovoltaic conversion efficiency is still about 11% (measuring using Method 2 described above). Therefore, to increase the photovoltaic conversion efficiency significantly in the art is very difficult. The dye-sensitized solar cell made using the ruthenium complex of the present invention has the photovoltaic conversion efficiency ranging from 11.10% to 11.81%, which is superior to that of Comparative Example 1 having the photovoltaic conversion efficiency being 10.05%. The improvement in the photovoltaic conversion efficiency is at least above 9.4%.

To sum up, the ruthenium complex according to this invention could absorb the light ranging from 400 nm to 600 nm in wavelength using the ligands $L^2$ and $L^3$ in the ruthenium complex. When the ruthenium complex is applied in a dye-sensitized solar cell, the short circuit current density of the dye-sensitized solar cell could be improved so as to increase the photovoltaic conversion efficiency.

While the present invention has been described in connection with what are considered the most practical and preferred embodiments, it is understood that this invention is not limited to the disclosed embodiments but is intended to cover various arrangements included within the spirit and scope of the broadest interpretation and equivalent arrangements.

What is claimed is:

1. A ruthenium complex for a dye-sensitized solar cell, comprising a chemical formula represented by Formula (I):

  (I)

where $L^1$ represents a monodentate ligand;

$L^2$ represents a tridentate ligand of

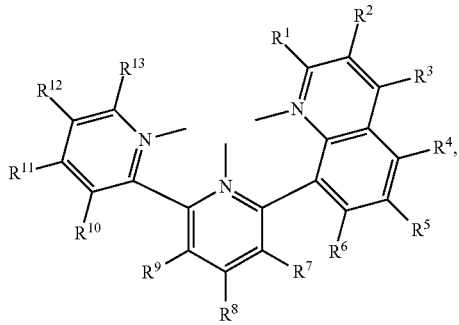

where $R^1$, $R^2$, $R^3$, $R^4$, $R^5$, and $R^6$ independently represent hydrogen, isobutyl,

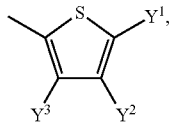

—$N(Ar)_2$, or —Ar—$N(Ar)_2$, where $Y^1$, $Y^2$, and $Y^3$ independently represent hydrogen, —$N(Ar)_2$, or —Ar—$N(Ar)_2$, and Ar represents an aryl group, and $R^7$, $R^8$, $R^9$, $R^{10}$, $R^{11}$, $R^{12}$, and $R^{13}$ independently represent hydrogen, halogen, trifluoromethyl, a $C_1$-$C_{12}$ straight chain alkyl group, a $C_1$-$C_{12}$ branched chain alkyl group, a phosphoric acid group, a phosphate group, a boric acid group, a borate group, a sulfonic acid group, a sulfonate group, a carboxylic acid group, or a carboxylate group with the proviso that at least two of $R^7$, $R^8$, $R^9$, $R^{10}$, $R^{11}$, $R^{12}$, and $R^{13}$ represent a carboxylic acid group or a carboxylate group;

and $L^3$ represents a bidentate ligand of

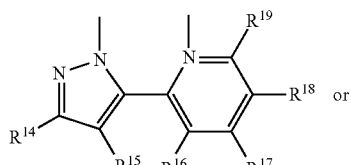 or

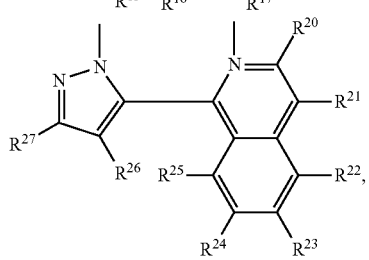

where $R^{14}$ and $R^{27}$ independently represent a fluoroalkyl group, and $R^{15}$, $R^{16}$, $R^{17}$, $R^{18}$, $R^{19}$, $R^{20}$, $R^{21}$, $R^{22}$, $R^{23}$, $R^{24}$, $R^{25}$, and $R^{26}$ independently represent hydrogen, isobutyl,

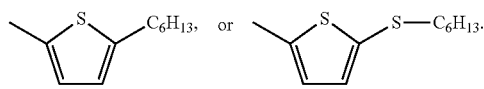

2. The ruthenium complex according to claim 1, wherein said fluoroalkyl group represents $C_nF_{2n+1}$, where n is an integer ranging from 1 to 7.

3. The ruthenium complex according to claim 1, wherein said monodentate ligand includes —N=C=S.

4. The ruthenium complex according to claim 1, wherein $R^1$, $R^2$, $R^3$, $R^4$, $R^5$, and $R^6$ are not hydrogen at the same time.

5. The ruthenium complex according to claim 1, wherein at least one of $R^{16}$, $R^{17}$, $R^{18}$, and $R^{19}$ is

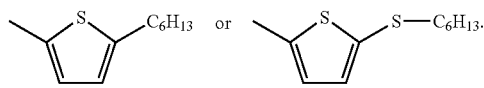

6. The ruthenium complex according to claim 1, wherein at least one of $R^{20}$, $R^{21}$, $R^{22}$, $R^{23}$, $R^{24}$, and $R^{25}$ represents isobutyl.

* * * * *